United States Patent
Yamamoto et al.

(10) Patent No.: US 6,183,459 B1
(45) Date of Patent: Feb. 6, 2001

(54) DISPOSABLE DIAPER

(75) Inventors: Masamitsu Yamamoto; Takamitsu Igaue, both of Kawanoe; Yoshihisa Fujioka, Kagawa-ken; Hirotomo Mukai, Kawanoe, all of (JP)

(73) Assignee: Uni-Charm Corporation, Ehime-ken (JP)

( * ) Notice: Under 35 U.S.C. 154(b), the term of this patent shall be extended for 702 days.

(21) Appl. No.: 08/690,402

(22) Filed: Jul. 25, 1996

Related U.S. Application Data

(63) Continuation of application No. 08/425,553, filed on Apr. 20, 1995, now abandoned.

(30) Foreign Application Priority Data

Apr. 21, 1994  (JP) .................................................. 6-082923

(51) Int. Cl.$^7$ ................................................ A61F 13/15
(52) U.S. Cl. .............................. 604/385.27; 604/385.28
(58) Field of Search ................................. 604/385.1–386, 604/389–391, 392, 394–397, 387, 393, 398–402, 373

(56) References Cited

U.S. PATENT DOCUMENTS

| | | | |
|---|---|---|---|
| Re. 33,106 | * 11/1989 | Beckestrom | 604/385.2 |
| 2,055,973 | * 9/1936 | Goss | 2/407 |
| 2,691,983 | * 10/1954 | Bernard | 604/401 |
| 3,882,871 | * 5/1975 | Taniguchi | 604/385.2 |
| 4,695,278 | 9/1987 | Lawson . | |
| 4,704,116 | * 11/1987 | Enloe | 604/385.2 |
| 4,738,677 | * 4/1988 | Foreman | 604/385.2 |
| 4,846,825 | 7/1989 | Enloe et al. . | |
| 4,904,251 | * 2/1990 | Igaue et al. | 604/385.2 |
| 5,026,364 | * 6/1991 | Robertson | 604/385.2 |
| 5,445,627 | * 8/1995 | Mizutani et al. | 604/387 |

FOREIGN PATENT DOCUMENTS

| | | | |
|---|---|---|---|
| 0098 512 | 1/1984 | (EP) . | |
| 0219 326 | 4/1987 | (EP) . | |
| 0 593 082 | 4/1994 | (EP) . | |
| 2250921 | 6/1992 | (GB) . | |
| 2271501 | * 4/1994 | (GB) | 604/385.2 |
| 4325153 | * 11/1992 | (JP) | 604/385.2 |
| 93/03744 | * 4/1993 | (WO) | 604/402 |
| 9410951 | * 5/1994 | (WO) | 604/385.2 |
| 95/08972 | 4/1995 | (WO) . | |

* cited by examiner

Primary Examiner—John G. Weiss
Assistant Examiner—K. M. Reichle
(74) Attorney, Agent, or Firm—Lowe Hauptman Gopstein Gilman & Berner

(57) ABSTRACT

A disposable diaper having a pair of cuffs longitudinally extending on the inner surface of the diaper along transversely opposite sides thereof across front and rear sections as well as a crotch section longitudinally interdisposed between these two sections, wherein each cuff has a substantially crescent-shaped elastic sheet bonded in its longitudinally stretched state to the inner surface along its longitudinally opposite ends and an outer arc defined between these ends.

7 Claims, 3 Drawing Sheets

DISPOSABLE DIAPER

This application is a continuation of application Ser. No. 08/425.553 filed Apr. 20, 1995, now abandoned.

BACKGROUND OF THE INVENTION

The present invention relates to a disposable diaper.

Disposable diapers are well known, in which a pair of cuffs longitudinally extend on the inner surface of the diaper along transversely opposite sides thereof and across front and rear sections as well as a crotch section. The pair of cuffs normally tend to rise above said inner surface to prevent body fluids from leaking laterally from the diaper.

FIG. 4 in the attached drawings is a plan view showing such a known disposable diaper as partially broken away. The diaper 100 has a basic body 105 comprising a liquid-permeable topsheet 102, a liquid-impermeable backsheet 103 and a liquid-absorbent core 104 sandwiched between these two sheets 102, 103 so as to form a front section 106, a rear section 107 and a crotch section 108 interposed between these two sections 106, 107 longitudinally of the diaper 100. A pair of water-repellent or liquid-impermeable cuffs 110 extend longitudinally along transversely opposite sides of the basic body 105 across the front and rear sections 106, 107 as well as the crotch section 108 so that these cuffs 110 may bear against the wearer's crotch as the diaper 100 is worn. Additionally, the basic body 105 is provided with elastic members (first elastic members) 116 extending along transversely opposite side edges thereof and bonded in their stretched states to the inner surface of the backsheet 103 for fitness around the respective legs of the wearer. A pair of tape fasteners 113 outwardly extend from transversely opposite side edges of the rear section 107. Each of the cuffs 110 comprises a rectangular strip of sheet having a width W. The cuff 110 has an inner side edge 115 which is a free edge and to which an elastic member (second elastic member) 114 is bonded in its longitudinally stretched state, and an outer side edge 117 extending parallel to the inner side edge 115. The outer side edge 117 and longitudinally opposite ends 118 of the cuff 110 are bonded, as indicated by oblique lines 120, to the inner surface of the diaper's basic body 105. When such diaper 100 is worn, the cuff 110 is biased under the contraction of the second elastic member 114 to rise above the topsheet 102 and to form together with the topsheet 102 a pocket (not shown) opening inwardly of the diaper 100. The cuff 110 forms a barrier of the height W against excretion as the cuff 110 rises substantially in the vertical direction in the crotch section 108. Such diaper 100 is disclosed, for example, in U.S. Pat. No. 4,695,278.

When worn, the diaper may slip down and cause a gap to be formed between the diaper and the wearer's crotch, possibly leading to excretion leakage. It is possible to avoid such excretion leakage if the cuffs form sufficiently high barriers when they rise. To achieve this with the above-mentioned known diaper 100, the width W may be dimensioned to be correspondingly large. However, such dimensioning would inevitably result in the longitudinally opposite ends 118 of the cuffs 110 bonded to the inner surface of the diaper 100 along the waist line becoming so bulky such that comfort deteriorates and, in the proximity of the waist line, the relatively wide cuffs 110 disadvantageously cover the topsheet 102 even when the cuffs 110 properly stand up in the crotch section 108. Consequently, the effective area of the topsheet 102 for liquid permeation is unacceptably reduced and thus desired rapid liquid permeation becomes difficult.

A accordingly, it is a principal object of the invention to solve the above-mentioned problems by providing substantially crescent-shaped cuffs made of a elastic sheets.

SUMMARY OF THE INVENTION

The object set forth above is achieved, according to the invention, by a disposable diaper comprising a liquid-permeable topsheet, a liquid-impermeable backsheet and a liquid-absorbent core sandwiched between these two sheets so as to form a front section, a rear section and a crotch section longitudinally interposed between these two sections, a pair of elasticized leg surrounding side flaps extending outwardly of transversely opposite sides of said core and a pair of elasticized cuffs longitudinally extending on the inner surface of said diaper along transversely opposite sides thereof across the front and rear sections as well as the crotch section and normally tending to rise on said inner surface, wherein each of said cuffs comprise a substantially crescent-shaped elastic sheet, bonded in its longitudinally stretched state to said inner surface at longitudinally opposite ends and along an arc-shaped outer edge of said cuff.

With the disposable diaper arranged as described above, there is no apprehension that the diaper might become bulky around the waist line even when the cuffs are dimensioned to be relatively large, since the cuffs are shaped in crescents, respectively, each having the width progressively reduced toward its longitudinally opposite ends.

PREFERRED EMBODIMENTS OF THE INVENTION

Figure 1:
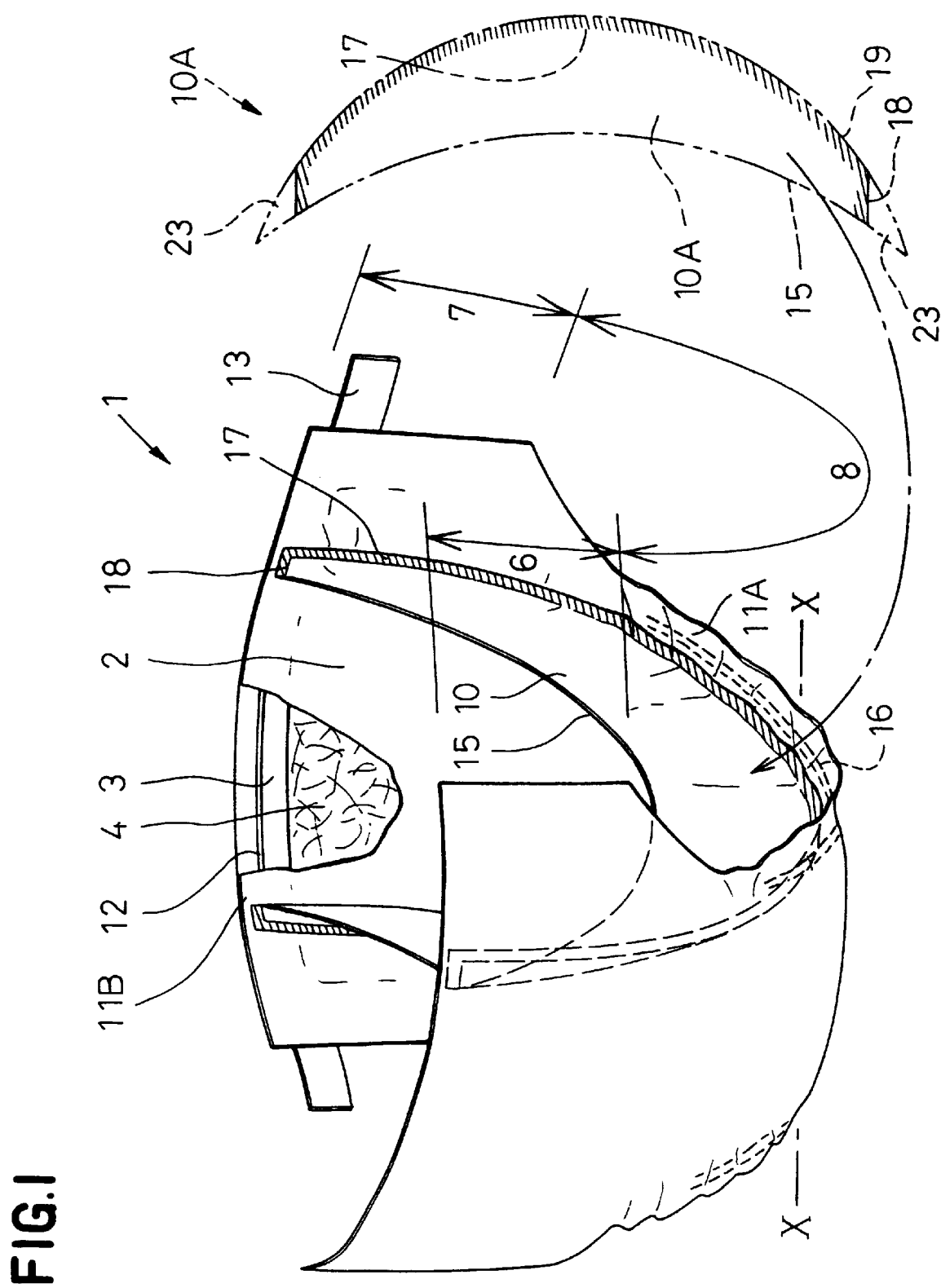
FIG. 1 is a perspective view showing an embodiment of a diaper according to the invention as partially broken away.
Figure 2:
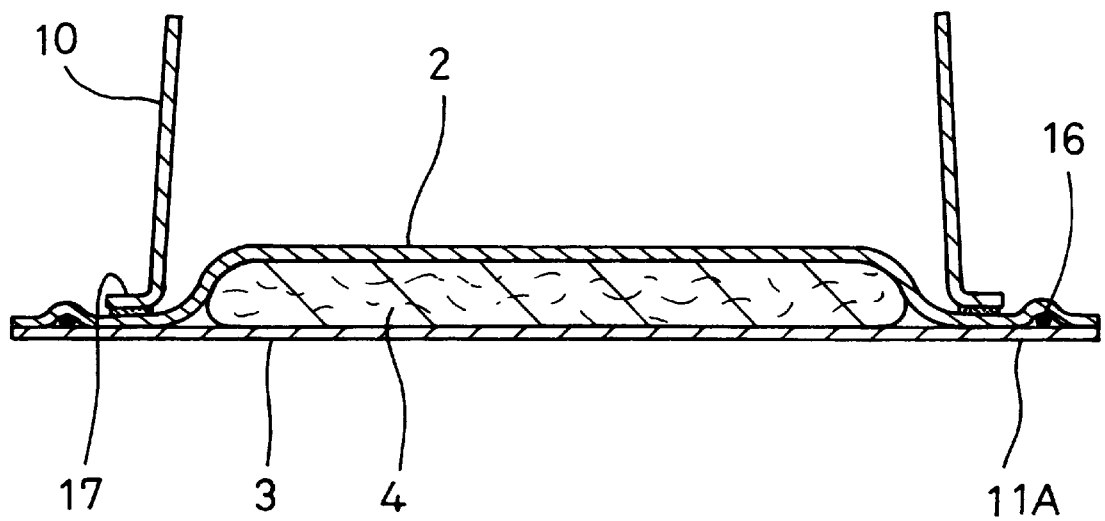
FIG. 2 is a sectional view taken along a line X—X in FIG. 1.

Referring to FIGS. 1 and 2, a diaper 1 comprises a liquid-permeable topsheet 2, a liquid-impermeable backsheet 3 and a liquid-absorbent core 4 sandwiched between these two sheets 2, 3. The top- and backsheets 2, 3 outwardly extend from the periphery of the liquid-absorbent core 4 and are bonded together in these outwardly extending regions to form leg surrounding flaps 11A and a waist surrounding flap 11B. The diaper 1 longitudinally composed of a front section 6, a rear section 7 and a crotch section 8 interposed between these two sections 6, 7. An elastic member (first elastic member) 12 is bonded in its stretched state to the inner surface of the backsheet 3 circumferentially along the waist surrounding flap 11B of the rear section 7, and a pair of tape fasteners 13 outwardly extend from transversely opposite side edges of the rear section 7, respectively. A pair of cuffs 10 longitudinally extend on the inlet surface of the diaper 1 along transversely opposite sides of the diaper 1 across the front and rear sections 6, 7 as well as the crotch section 8 so that these cuffs 10 may bear against the wearer's crotch as the diaper 1 is worn. Each leg surrounding flap 11A is cut away to form an arc-shaped notch outside the associated cuff 10 and an elastic member (second elastic member) 16 is bonded in its stretched state to the inner surface of the backsheet 3 in parallel to and inside the arc.

Reference numeral 10A in FIG. 1 designates each cuff 10 shown in a plan view before it is bonded to the inner surface of the diaper 1. The cuff 10A is made of a crescent-shaped strip of elastic sheet and preferably has its upper and lower ends as viewed in FIG. 1 (i.e., longitudinally opposite ends with respect to the diaper 1) 23 cut away and bonded to the inner surface of the diaper 1 along a bonding margin 17 as indicated by oblique lines so as to obtain the cuff 10 adapted to rise on its new ends 18 as well as an outer arc 19 defined between these new ends 18. It should be understood here that a linear distance between the ends 18 of the cuff 10A is dimensioned to be shorter than a linear distance between longitudinally opposite ends of the diaper 1 and the cuff 10A is bonded to the inner surface of the diaper so that the topsheet 2 may be curved in accordance with the outer arc 19 or the cuff 10A is bonded in its appropriately stretched state to the inner surface of the diaper 1 at the desired region. With the diaper 1 having such cuff 10, the cuff 10 is normally biased under its elastic contraction to rise so that the diaper 1 is curved with its inner surface in a concave shape and with an inner arc 15 of the cuff 10 serving as a free edge bearing against the wearer's crotch. The cuff 10 configured substantially in the crescent-shape allows the height of the risen cuff 10 to be maximized in the crotch section 8 and progressively reduced toward the front and rear sections 6, 7, leaving only the negligibly small bonding margins at the longitudinally opposite ends 11B of the diaper 1. Such cuff 10 is comfortable to wear, since it does not make the diaper 1 bulky in the proximity of the longitudinally opposite ends 11B of the diaper 1.

Figure 3:
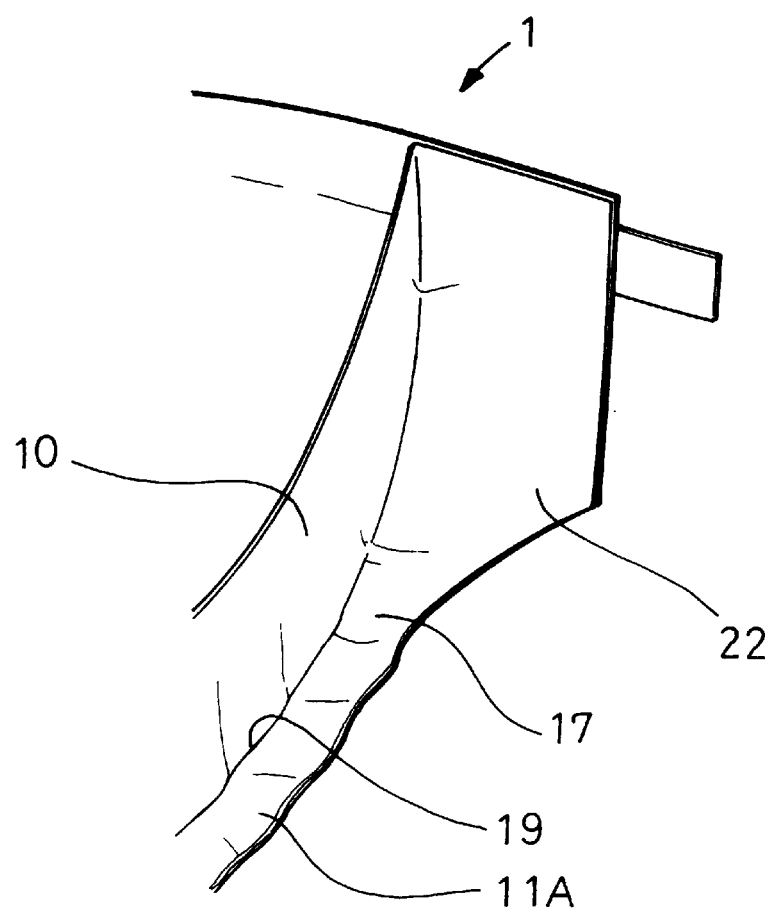
FIG. 3 is a perspective view showing part of a diaper as a variant of the diaper in FIG. 1.
Figure 4:
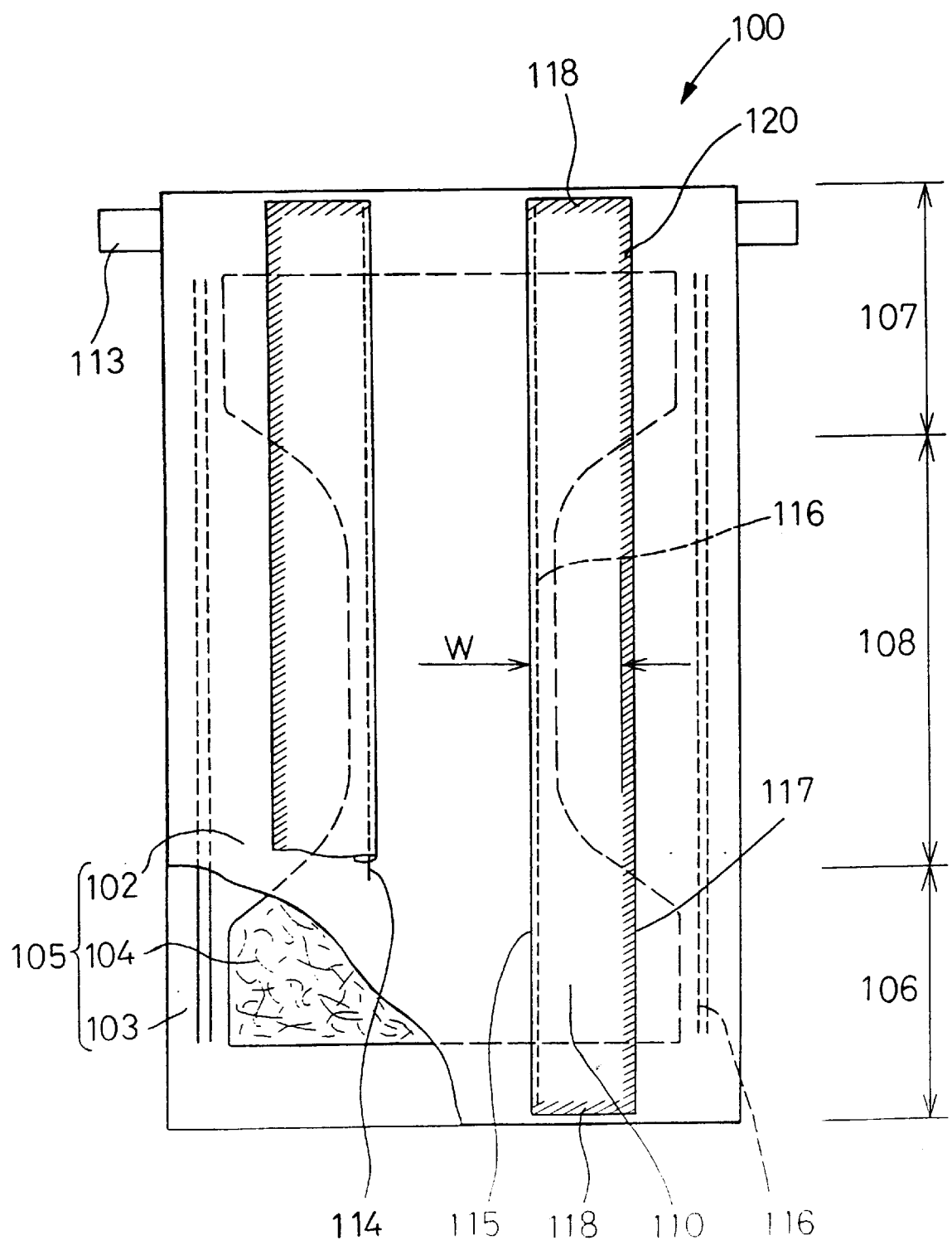
FIG. 4 is a plan view showing a prior art diaper as partially broken away.

Referring to FIG. 3, while the cuff 10 is configured substantially in a crescent-shape, the bonding margin 17 along which the cuff 10 is bonded to the inner surface of the diaper 1 is dimensioned to be sufficiently large to cover the leg surrounding flap 11A as well as wings 22 of the front and rear sections 6, 7 and to define a substantially same outline as that of the diaper 1. Such a configuration of the cuff 10 is preferable when there is an apprehension that the bonding margin 17 of the cuff 10 bonded to the topsheet 2, in the embodiment of FIG. 1 might make a difference in thickness making such undesirable for wearing comfort or that body fluids diffused in the plane of the topsheet 2 might ooze out on the surfaces of the leg surrounding flap 11A and the wings 22.

For the invention, the cuff 10 may be made by an elastic sheet material such as an elastic nonwoven fabric of composite fibers or melt blown fibers or an elastic plastic film, for example, an elastomeric film. Such sheet materials are preferably water-repellent, liquid-impermeable or air-permeable but liquid-impermeable. The top- and backsheets 2, 3 and the other members may be made of materials usually employed in this technical field and, for bonding of these members, adhesive such as hot melt adhesive, gluing agent and welding technique may be employed.

With the disposable diaper of the invention, the configuration of the cuff substantially in crescent-shape allows the height of the risen cuff to be relatively high without the apprehension that the longitudinally opposite ends of the diaper is unduly bulky due to such dimensioning and thus significantly improves the wearing comfort compared to the prior art.

What is claimed is:

1. A disposable diaper comprising:
   a liquid-permeable topsheet;
   a liquid-impermeable backsheet;
   a liquid-absorbent core sandwiched between said topsheet and said backsheet;
   said topsheet, said backsheet, and said core defining a front section, a rear section and a crotch section of said diaper, said crotch section longitudinally interposed between said front section and said rear section;
   a pair of elasticized side flaps formed by portions of said topsheet and said backsheet extending outwardly of transversely opposite sides of said core; and
   a pair of elasticized cuffs extending longitudinally along transversely opposite sides of an inner surface of said topsheet across said front section, said crotch section, and said rear section, each of said pair of elasticized cuffs extending above said inner surface, each of said pair of elasticized cuffs being made of an elastic sheet being elastic throughout and including a substantially crescent-shaped portion having an arc-shaped outer edge and longitudinally opposite ends and a bonding zone extending outwardly from said arc-shaped outer edge, each of said pair of elasticized cuffs being bonded in a longitudinally stretched state to said inner surface at said longitudinally opposite ends and along said bonding zone, and said bonding zone covering at least a portion of an area of said side flap extending outwardly from said arc-shaped outer edge.

2. A disposable diaper according to claim 1, wherein:
   each of said elasticized side flaps has an outer side edge;
   each of said elasticized side flaps includes a first elastic member disposed longitudinally adjacent said outer side edge of an associated one of said side flaps; and
   each of said elasticized cuffs are disposed inwardly from a respective one of said first elastic members.

3. A disposable diaper according to claim 1, wherein said bonding zone substantially covers each of said elasticized side flaps.

4. A disposable diaper according to claim 1, wherein said longitudinally opposite ends of said substantially crescent-shaped portion are truncated.

5. A disposable diaper according to claim 1, wherein:
   said diaper has longitudinally opposite ends; and
   said longitudinally opposite ends of said substantially crescent-shaped portion extend to said longitudinally opposite ends of said diaper.

6. A disposable diaper comprising:
   a liquid-permeable topsheet;
   a liquid-impermeable backsheet;
   a liquid-absorbent core sandwiched between said topsheet and said backsheet;
   said topsheet, said backsheet, and said core defining a front section, a rear section and a crotch section of said diaper, said crotch section longitudinally interposed between said front section and said rear section;
   a pair of elasticized side flaps formed by portions of said topsheet and said backsheet extending outwardly of transversely opposite sides of said core; and
   a pair of elasticized cuffs extending longitudinally along transversely opposite sides of an inner surface of said topsheet across said front section, said crotch section, and said rear section, each of said pair of elasticized cuffs extending above said inner surface, each of said pair of elasticized cuffs being made of an elastic sheet being elastic throughout and including a crescent-shaped portion having an arc-shaped outer edge and longitudinally opposite ends and a bonding zone extending outwardly from said arc-shaped outer edge, each of said pair of elasticized cuffs being bonded in a longitudinally stretched state to said inner surface at said longitudinally opposite ends and along said bond ing zone, and said bonding zone covering at least a portion of an area of said side flap extending outwardly from said arc-shaped outer edge.

7. A disposable diaper according to claim 6, wherein:

said diaper has longitudinally opposite ends; and
said longitudinally opposite ends of said crescent-shaped portion extend to said longitudinally opposite ends of said diaper.

* * * * *